United States Patent
Stearns (10) Patent No.: US 6,462,342 B1
(45) Date of Patent: Oct. 8, 2002

(54) METHOD AND SYSTEM FOR PET IMAGE RECONSTRUCTION

(75) Inventor: Charles W. Stearns, New Berlin, WI (US)

(73) Assignee: GE Medical Systems Global Technology Co. LLC, Waukesha, WI (US)

(*) Notice: Subject to any disclaimer, the term of this patent is extended or adjusted under 35 U.S.C. 154(b) by 204 days.

(21) Appl. No.: 09/602,104

(22) Filed: Jun. 22, 2000

(51) Int. Cl.$^7$ .............................................. G01T 1/166
(52) U.S. Cl. .............................. 250/363.03; 250/363.04
(58) Field of Search ....................... 250/363.03, 363.02, 250/363.01, 363.04, 370.09; 378/4, 21

(56) References Cited

U.S. PATENT DOCUMENTS

| | | | | |
|---|---|---|---|---|
| 5,331,553 A | * | 7/1994 | Muehllehner et al. | 250/363.02 |
| 5,404,293 A | * | 4/1995 | Weng et al. | 378/15 |
| 5,424,946 A | * | 6/1995 | Stearns | 250/363.03 |
| 5,543,622 A | * | 8/1996 | Stearns | 250/363.03 |
| 5,703,369 A | * | 12/1997 | Mori | 250/363.03 |
| 5,744,802 A | * | 4/1998 | Muehllehner et al. | 250/363.03 |
| 6,332,035 B1 | * | 12/2001 | Basu et al. | 378/4 |

OTHER PUBLICATIONS

M. Defrise, P. Kinahan, D. Townsend, *A New Rebinning Algorithm for 3D Pet: Principle, Implementation and Performance*, Proceedings of : 1995 International Meeting on Fully Three–dimensional Image Reconstruction in Radiology and Nuclear Medicine, Aix–les–Bains, France, Jul. 4–5: pp. 235–239, 1995.

M. Defrise, *A Factorization Method for the 3D X–ray Transform*, Inverse Problems 11, pp. 983–994 (1995).

P.E. Kinahan and J.G. Rogers, *Analytic 3D Image Reconstruction Using All Detected Events,* IEEE Transactions on Nuclear Science 36, pp. 964–968 (Feb. 1989).

P.R. Edholm, R.M. Lewitt, B. Lindholm, *Novel Properties of the Fourier Decomposition of the Sinogram,* SPIE 671 Physics and Engineering of Computerized Multidimensional Imaging and Processing, pp. 8–18 (1986).

M. Defrise, M. Sibomana, C. Michel, D. Newport, *3D PET Reconstruction with the ECAT EXACT HR Using Fourier Rebinning,* Proceedings of: IEEE Medical Imaging Conference, San Francisco Oct. 21–28, 1995, pp. 1316–1320.

* cited by examiner

Primary Examiner—Constantine Hannaher
Assistant Examiner—Albert Gagliardi
(74) Attorney, Agent, or Firm—Quarles & Brady LLP (57) ABSTRACT

A method and system for processing data in a PET scanner is provided, in which a projection plane data set is converted into a two-dimensional sinogram data set. The method includes (1) selecting a subset of projection plane data from the projection plane data set, (2) performing a set of Fourier transforms, respectively, on a plurality of data rows within the subset of projection plane data to obtain a transformed data set, and (3) performing an additional set of Fourier transforms on the transformed data set to obtain intermediate results. The additional set of Fourier transforms includes a plurality of individual Fourier transforms respectively corresponding to a plurality of combinations of at least two indices. The method additionally includes (4) rebinning the intermediate results into a first array, the first array having at least a first dimension corresponding to a physical dimension of the PET scanner, (5) repeating (1)–(4) for each of the remaining subsets of projection plane data, to provide a complete data set within the first array, and (6) performing a set of inverse Fourier transforms with respect to the complete data set to provide the two-dimensional sinogram data set.

18 Claims, 4 Drawing Sheets

FIG. 6

METHOD AND SYSTEM FOR PET IMAGE RECONSTRUCTION

BACKGROUND OF THE INVENTION

The field of the invention is positron emission tomography (PET) scanners, and particularly volumetric or hybrid PET scanners which organize volumetric PET data as a set of projection planes $p_{\theta,\phi}(r,v)$.

Positrons are positively charged electrons which are emitted by radionuclides that have been prepared using a cyclotron or other device. These a re employed as radioactive t racers called "radiopharmaceuticals" by incorporating them into substances, such as glucose or carbon dioxide. The radiopharmaceuticals are injected in the patient and become involved in such processes as blood flow, fatty acid, glucose metabolism, and protein synthesis. As the radionuclides decay, they emit positrons. The positrons travel a very short distance before they encounter an electron, and when this occurs, they are annihilated and converted into two photons, or gamma rays. This annihilation is characterized by two features which are pertinent to PET scanners—each gamma ray has an energy of 511 keV and the two gamma rays are directed in nearly opposite directions. An image is created by determining the number of such annihilations at each location within the field of view.

The PET scanner is cylindrical and includes a detector ring assembly composed of rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events (coincidence events) indicates the number of positron annihilations that occurred along a line joining the two opposing detectors. Within a few minutes hundreds of millions of coincidence events are recorded to indicate the number of annihilations along lines joining pairs of detectors in the detector ring. These numbers are employed to reconstruct an image using well-known computed tomography techniques.

When originally developed, PET scanners were strictly multiplanar scanners. In such PET scanners, each detector ring is configured to only detect annihilations occurring within (i.e., within the plane of) that respective ring alone, and not to detect annihilations occurring at other positions within the PET scanner (i.e., annihilations occurring within the other rings of the PET scanner). Because e each detector within each detector ring is capable of receiving photons coming in toward the detector from a variety of angles (rather than merely coming in toward the detector from the center of the ring of which the detector is a part), fixed slice septa are positioned in between each of the detector rings of the PET scanners. The septa, which are commonly composed of lead or tungsten alloy, shield the detectors of each individual detector ring from photons that have not originated from annihilations within the ring, and from scattered photons or other photons that are not resulting from annihilations (i.e., photons entering at either end of the cylindrical PET scanner). Multiplanar data can be organized as a set of two-dimensional sinograms $p_z(r,\phi)$.

A major innovation in PET scanners that occurred in the late 1980s and early 1990s was the development of volumetric, or true-3D, PET scanners. In contrast to multiplanar scanners, volumetric PET scanners have no septa and consequently the detectors of each detector ring of the scanners can receive photons from a wider range of angles with respect to the plane of the respective ring than in multiplanar PET scanners. Volumetric PET scanners became feasible partly as a result of the increased speed of computers generally, since volumetric PET imaging requires determining the existence of, and processing information related to, coincidence events that occur not merely between pairs of detectors positioned on individual (or adjacent) detector rings, but also between pairs of detectors positioned on detector rings that are spaced more than one ring apart. Volumetric PET scanners allow for increased sensitivity relative to multiplanar scanners, since more coincidence events can be recorded. However, volumetric PET scanners also admit more scattered and random coincidence events to the data set from which the image is reconstructed than multiplanar PET scanners.

Most medium-end and high-end PET scanners available on the market today, including the GE Advance PET scanner manufactured by General Electric Company of Waukesha, Wisconsin, have septa which are automatically retractable. Through the use of such automatically retractable septa, the PET scanners are able to operate as volumetric PET scanners (with the septa retracted) when the benefits associated with increased sensitivity due to volumetric PET scanning outweigh the loss in data quality resulting from the detection of more scattered and random coincidence events. This is typically the case, for example, when the PET scanners are used for brain imaging purposes. However, the PET scanners are also able to operate as multiplanar PET scanners (with the septa extended) when the loss of data quality due to the detection of scattered and random coincidence events becomes excessive. This is typically the case, for example, when the PET scanners are used for body imaging purposes. Thus, PET scanners with automatically retractable septa are "hybrid" PET scanners in that the PET scanners can operate both as multiplanar and volumetric PET scanners depending upon the positioning of the septa.

The amount of data produced by a volumetric PET scanner or a hybrid PET scanner operating in volumetric mode is much greater than that produced by a multiplanar PET scanner. While multiplanar PET data can be described in terms of three variables r,$\phi$ and z and thus be organized as a set of two-dimensional sinograms, volumetric PET data from either a volumetric PET scanner or a hybrid PET scanner typically is described in terms of four variables r, v, $\theta$ and $\phi$. Processing of the data from a volumetric PET scanner is therefore much more complicated and time-consuming than processing of the data from a hybrid PET scanner. However, various techniques have been developed to reduce the complexity of, and time required for, processing volumetric PET data.

One such technique is Fourier Rebinning (FORE), which employs an algorithm developed by Michel Defrise and others and is described in publications such as "A new rebinning algorithm for 3D PET: Principle, implementation and performance." by M. Defrise, P. Kinahan and D. Townsend, in *Proceedings of the 1995 International Meeting on Fully Three-Dimensional Image Reconstruction in Radiology and Nuclear Medicine*, pp 235–239, July 1995. The mathematical foundation of the FORE algorithm is an extension of the frequency-distance principle, which relates the two-dimensional discrete Fourier transform (DFT) of the cross-plane sinogram $p_{v,\theta}(r,\phi)$ to the set of two-dimensional sinograms $p_z(r,\phi)$. That is, through the use of the FORE algorithm, the four-dimensional volumetric PET data can be effectively reduced to a more manageable set of two-dimensional sinograms.

In order to apply the FORE algorithm, it is necessary for the volumetric PET data to be organized as a set of cross-plane sinograms $p_{v,\theta}(r,\phi)$. In many PET scanners including the GE Advance, however, volumetric PET data is organized as a set of projection planes $p_{\theta,\phi}(r,v)$, with $\theta$ as the slowest changing variable. The volumetric PET data is organized in this fashion because the PET scanners are designed to perform corrections on the data in the projection plane format, among other reasons. Because the volumetric PET data is organized in projection plane format, it is necessary to resort the data into the cross-plane sinogram format in order to perform the FORE algorithm on this data. That is, it is necessary to resort data in the form of $p_{\theta,\phi}(r,v)$ into data in the form of $p_{v,\theta}(r,\phi)$.

This resorting of data from the projection plane format into the cross-plane sinogram format is a very time-consuming operation. The resorting of data typically involves writing the data set to disk and then reading it back in sorted form, which is a slow process. Moreover, the volumetric PET data set is typically very large. For example, in the GE Advance PET scanner, a volumetric PET data set includes approximately 25 million elements and requires nearly 100 MB of memory. Because of the size of the volumetric PET data set, the resorting process is particularly time-consuming.

It therefore would be advantageous to develop a method and apparatus for applying the FORE algorithm to data that is originally received in the projection plane format in which it was not necessary to resort the data from the projection plane format into the cross-plane sinogram format.

SUMMARY OF THE INVENTION

It has been discovered that an angular portion of the data obtained in the projection plane format can be decimated in a particular manner so that portions of the total amount of data can be read into memory, sorted into sinogram fragments, operated on by way of reduced-length two-dimensional discrete Fourier transforms, and then added together to obtain a set of two dimensional sinograms. The two-dimensional sinograms obtained from the operation are the same set of sinograms as would be obtained by resorting the data from the projection plane format into the cross-plane sinogram format and then performing the FORE algorithm upon that cross-plane sinogram data.

The present invention relates to a method of processing data in a PET scanner in which a projection plane data set is converted into a two-dimensional sinogram data set. The method includes (1) selecting a subset of projection plane data from the projection plane data set, (2) performing a set of Fourier transforms, respectively, on a plurality of data rows within the subset of projection plane data to obtain a transformed data set, and (3) performing an additional set of Fourier transforms on the transformed data set to obtain intermediate results. The additional set of Fourier transforms includes a plurality of individual Fourier transforms respectively corresponding to a plurality of combinations of at least two indices. The method further includes (4) rebinning the intermediate results into a first array, the first array having at least a first dimension corresponding to a physical dimension of the PET scanner, (5) repeating (1)–(4) for each of the remaining subsets of projection plane data, to provide a complete data set within the first array, and (6) performing a set of inverse Fourier transforms with respect to the complete data set to provide the two-dimensional sinogram data set.

The present invention further relates to an additional method of processing data in a PET scanner in which input data in a projection plane format is converted into output data in a two-dimensional sinogram format. The additional method includes (1) performing a Fourier transform of a plurality of data rows within a projection plane data set to obtain a transformed data set, (2) setting a first index, a second index and a third index equal to first, second and third initial values, respectively, and (3) calculating a first array, based upon the values of the first, second and third indices. The method further includes (4) setting a fourth index equal to a fourth initial value, (5) performing a Fourier transform of each column of the first array to obtain a second array, (6) rebinning the data of the second array into a third array, and (7) incrementing the value of the fourth index. The method additionally includes (8) repeating (5)–(7) until the value of the fourth index has reached a fourth limit, (9) incrementing the values of the first, second and third indices, and (10) repeating (3)–(9) until the values of the first, second and third indices have reached first, second and third limits, respectively.

The present invention additionally relates to a PET scanner including a gantry, a plurality of sets of detectors supported by the gantry, and a coincidence detector. The detectors in each set are disposed in a plane and positioned around a central axis that intersects the plane, and the plurality of sets of detectors are spaced along the central axis. The coincidence detector identifies coincidence events from events sensed by the detectors, and is configured to provide coincidence event data in a projection plane format. The PET scanner further includes a processing means for converting the coincidence event data from the projection plane format directly into a two-dimensional sinogram format without conversion of the data from the projection plane format into a cross-plane sinogram format.

The present invention further relates to an array processor including a first array and a second array. In the first array, first and second subsets of transformed row data corresponding respectively to positive and negative values of a first index are stored. The transformed row data is obtained by performing a first set of Fourier transforms with respect to a set of projection plane data. In the second array, the results of a second set of Fourier transforms performed upon the transformed row data are rebinned. The second set of Fourier transforms includes individual Fourier transforms corresponding to each respective combination of a second index and a third index.

DESCRIPTION OF THE PREFERRED EMBODIMENT

Figure 1:
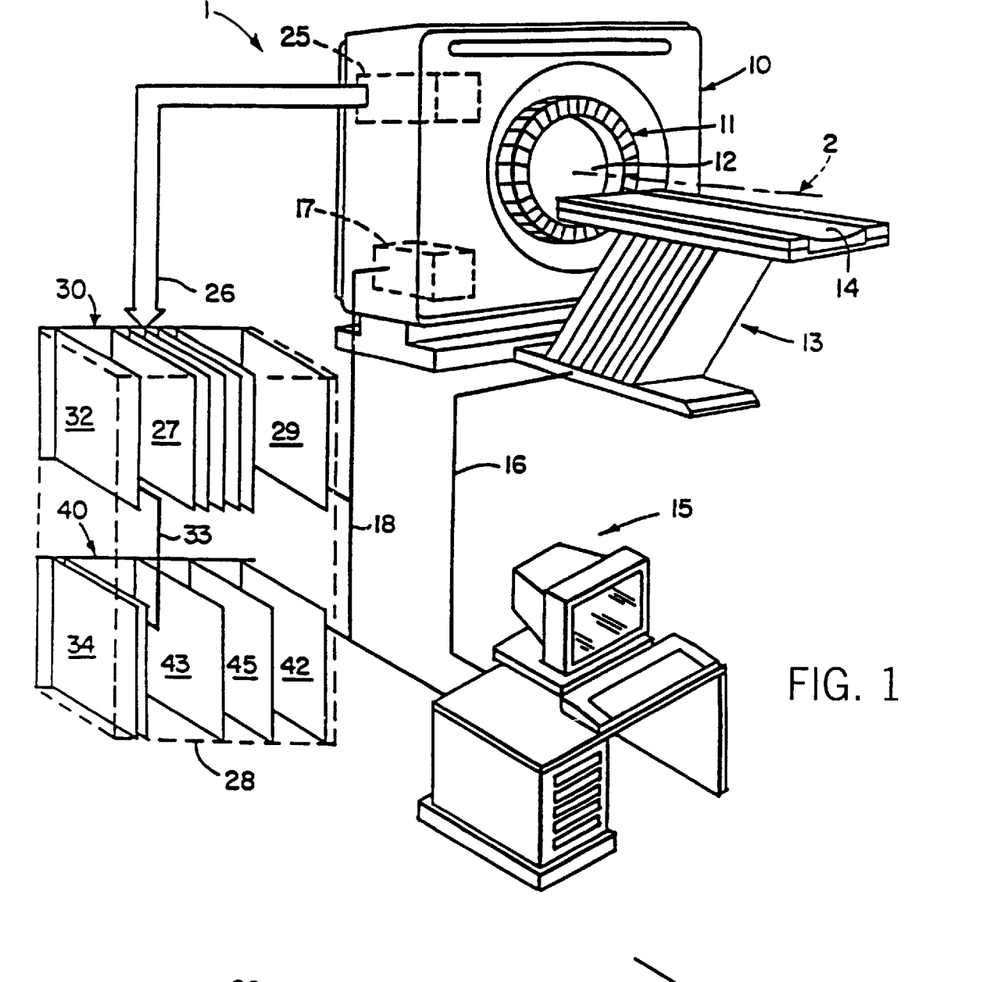
FIG. 1 is a pictorial view with parts cut away of a PET scanner system which employs the present invention.

Referring particularly to FIG. 1, a volumetric or hybrid PET scanner 1 is shown. The PET scanner 1 includes a gantry 10 which supports a detector ring assembly 11 about a central opening, or bore 12. The detector ring assembly 11 is circular in shape, and is made up of multiple detector rings (not shown) that are spaced along a central axis 2 to form a cylindrical detector ring assembly. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a second serial communication link 18 to operate the gantry.

Figure 2:
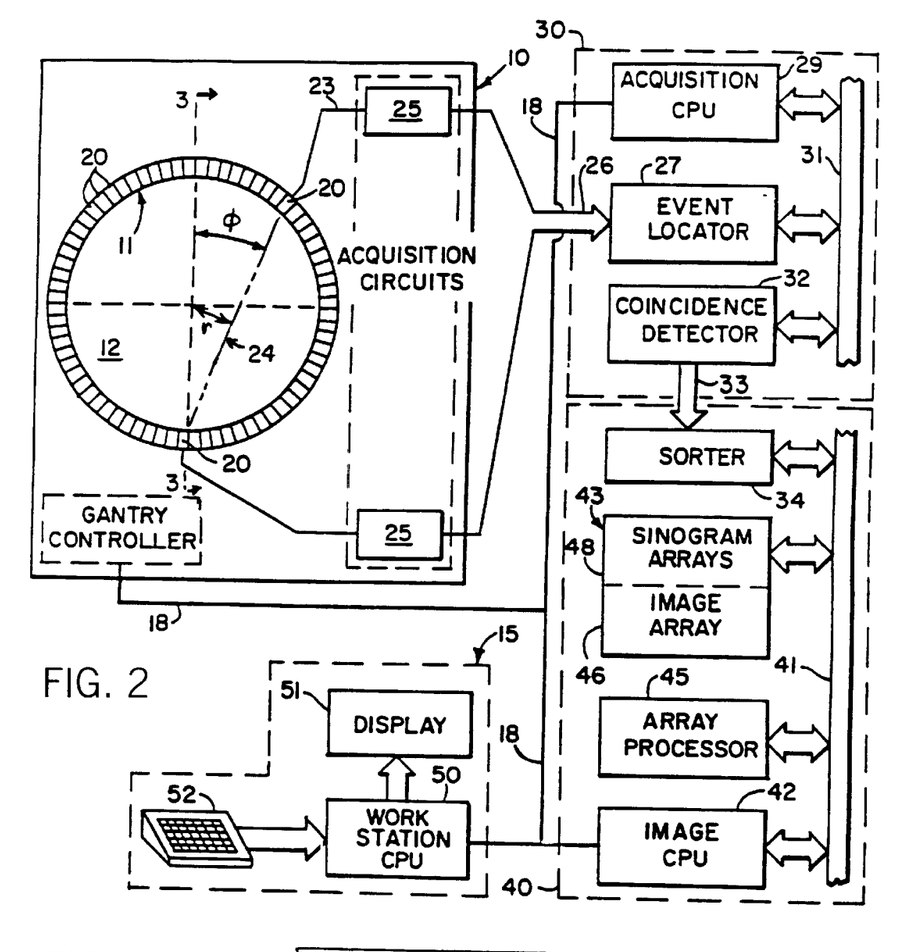
FIG. 2 is a schematic diagram of the PET scanner system of FIG. 1.
Figure 4:
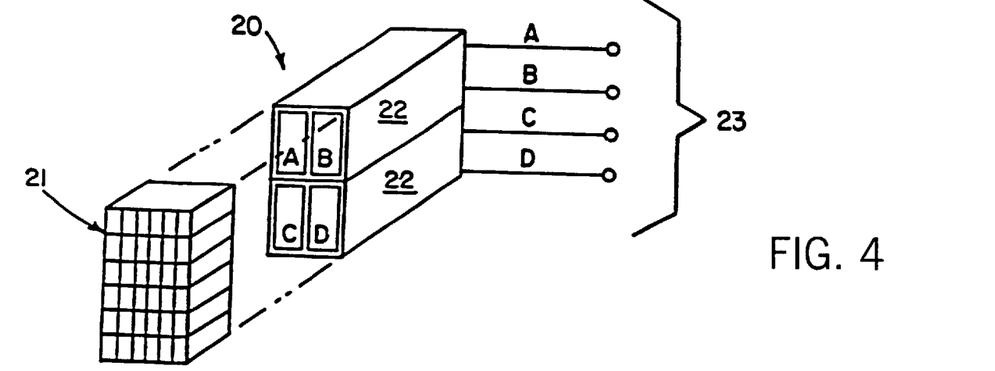
FIG. 4 is a pictorial view of a detector unit which forms part of the PET scanner system of FIG. 1.

As shown best in FIG. 2, each detector ring of the detector ring assembly 11 is comprised of detectors 20. Each detector 20 includes a scintillator or BGO crystal 21. Each BGO crystal 21 is disposed in front of a photomultiplier tube 22 (abbreviated PMT). More than one BGO crystal 21 may be disposed in front of a given PMT 22. For example, in one embodiment (shown in FIG. 4) a matrix of 36 BGO crystals 21 is disposed in front of four PMTs 22, such that 9 BGO crystals are disposed in front of each of the PMTs. All of the PMTs 22 produce analog signals on line 23 when a scintillation event occurs at one of the 36 BGO crystals 21 that are disposed in front of the PMTs (i.e., when a photon is received by one of the BGO crystals 21). A set of acquisition circuits 25 is mounted within the gantry 10 to receive these signals and produce digital signals indicating the event coordinates (x,y) and the total energy. These are sent through a cable 26 to an event locator circuit 27 housed in a separate cabinet 28. Each acquisition circuit 25 also produces an event detection pulse (EDP) which indicates the exact moment the scintillation event took place.

Referring particularly to FIG. 2, the event locator circuits 27 form part of a data acquisition processor 30 which periodically samples the signals produced by the acquisition circuits 25. The processor 30 has an acquisition CPU 29 which controls communications on the local area network 18 and a backplane bus 31. The event locator circuits 27 assemble the information regarding each valid event into a set of digital numbers that indicate precisely when the event took place and the position of the detector 20/crystal 21 which detected the event. This event data packet is conveyed to a coincidence detector 32 which is also part of the data acquisition processor 30.

The coincidence detector 32 accepts the event data packets from the event locators 27 and determines if any two of them are in coincidence. 10 Coincidence is determined by a number of factors. First, the time markers in each event data packet must be within 12.5 nanoseconds of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. For a detailed description of the coincidence detector 32, reference is made to U.S. Pat. No. 5,241,181 entitled "Coincidence Detector For A PET Scanner" which is incorporated herein by reference.

Figure 3:
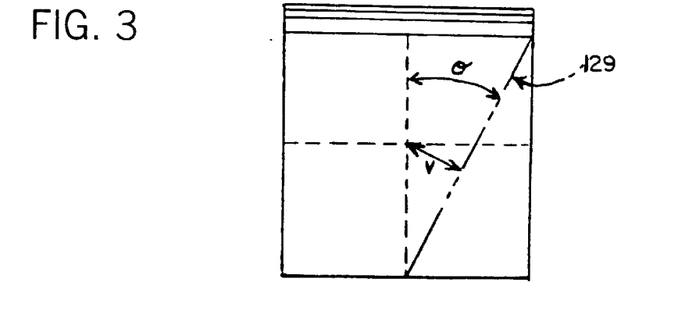
FIG. 3 is a partial cross-section taken through a detector ring assembly in the PET scanner system of FIG. 1.

Each pair of event data packets that is identified by the coincidence detector 32 is described in a projection plane format using four variables r, v, θ and φ, i.e., according to the form $p_{\theta,\phi}(r,v)$. As shown in FIG. 2, the variables r and φ identify a plane 24 that is parallel to the central axis 2, with φ specifying the angular direction of the plane with rescect to a reference plane and r specifying the distance of the central axis from the plane as measured perpendicular to the plane. As further shown in FIG. 3, the variables v and θ further identify a particular line 129 within that plane 24, with θ specifying the angular direction of the line within the plane, relative to a reference line within the plane, and v specifying the distance of the central point from the line as measured perpendicular to the line.

The sorter 34 forms part of an image reconstruction processor 40. The sorter 34 counts all events occurring along each projection ray (r, v, θ and φ), and stores that information in the projection plane format. The image reconstruction processor 40 also includes an image CPU 42 that controls a backplane bus 41 and links it to the local area network 18. An array processor 45 also connects to the backplane bus 41. The array processor converts the event information stored by the sorter 34 into a two dimensional sinogram array 48 ($p_z(r,\phi)$) which is stored in a memory module 43. As discussed further below, the array processor 45 converts the data from the projection plane format into the two-dimensional sinogram format without intermediate conversion to the cross-plane sinogram format. Upon conversion of the data into the two-dimensional sinogram format, images can be constructed. The resulting image array 46 is also stored in the memory module 43 and is output by the image CPU 42 to the operator work station 15. For a detailed description of the sorter 34, reference is made to U.S. Pat. No. 5,272,343 entitled "Sorter For Coincidence timing Calibration In A PET Scanner" which is incorporated herein by reference.

The operator work station 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. Similarly, the operator can control the display of the resulting image on the CRT display 51 and perform image enhancement functions using programs executed by the work station CPU 50.

In accordance with the present invention, data obtained in the projection plane format is converted into the two-dimensional sinogram format without intermediate conversion into the cross-plane sinogram format. To avoid the need for conversion from the projection plane format into the cross-plane sinogram format, the present invention employs a new decimation technique in performing the discrete Fourier transforms (DFTs) that are the key component of the FORE algorithm. Conventional decimation techniques take a DFT of length N and decompose it into Z DFT's of length N/Z. Specifically, the decimation-in-time algorithm computes DFTs of subsequences of every Zth point from the input sequence (e.g., the sequences [X(0), X(Z), . . . ], [X(1), X(Z+1), . . . ], etc.), while the decimation-in-frequency algorithm combines every N/Z'th point from the input sequence to form its subsequences (e.g., the first portion of the decimation-in-frequency algorithm with Z=2 transforms the sequence [X(0)+X(N2),X(1)+X(N/2+1), . . . ]). These conventional decimation techniques are inapplicable to the projection plane data set because the transaxial angle data is such that the data sequence for the DFT in the angular direction is X(0),X(N/2),X(1),X(N/2+1), . . .

Given the inadequacy of such conventional decimation techniques, the present invention employs a decimation technique in which the transform sequence X(k) is divided into odd and even elements by the variable s, which takes on values of 0 or 1. The odd- and even-element sub-sequences are further decimated by the variables q (which takes on values from 0 though Z−1) and p (values 0 through N/Z−1). The 2pZ+2q+s'th element of the output sequence is the sum of the p'th element of Z DFT's of length N/2Z:

$$X(2pZ+2q+s) = \sum_{y=0}^{Z-1} DFT_{N/2Z}\left\{\left[X\left(\frac{yN}{2Z}+n\right)+(-1)^s X\left(\frac{N}{2}+\frac{yN}{2Z}+n\right)\right]W_N^{(\frac{yN}{2Z}+n)(2q+s)}\right\} \quad (1)$$

Equation (1) is derived by starting with the definition of the DFT:

$$X(k) = DFT_N\{x(n)\} = \sum_{n=0}^{N-1} x(n) W_N^{nk} \quad (2)$$

where the "twiddle factor" $W_N^a$ is defined as $e^{31\, j2\pi a/N}$. Next, a standard decimation-in-frequency of the Fourier transform computation is begun by combining the first half and second half of the input sequence:

$$X(k) = \sum_{n=0}^{\frac{N}{2}-1}\left[x(n)W_N^{nk} + x\left(\frac{N}{2}+n\right)W_N^{(\frac{N}{2}+n)k}\right] \quad (3)$$

$$= \sum_{n=0}^{\frac{N}{2}-1}\left[x(n) + x\left(\frac{N}{2}+n\right)W_N^{\frac{N}{2}k}\right]W_N^{nk}$$

The odd and even output values are then considered separately through the substitutions k=2r+s, where s=0 or 1, and r∈[0,N/2]:

$$X(2r+s) = \sum_{n=0}^{\frac{N}{2}-1}\left[x(n) + x\left(\frac{N}{2}+n\right)W_N^{\frac{N}{2}(2r+s)}\right]W_N^{n(2r+s)} \quad (4)$$

$$= \sum_{n=0}^{\frac{N}{2}-1}\left[x(n) + x\left(\frac{N}{2}+n\right)W_N^{rN}W_N^{s\frac{N}{2}}\right]W_N^{ns}W_N^{2nr}$$

The twiddle factor $W_N^a$ has particular properties, including that $W_N^{KN} = 1$, $W_{aN}^{aK} = W_N^K$, and $W_2^1 = -1$. Using these properties, equation (4) can be reduced to:

$$X(2r+s) = \sum_{n=0}^{\frac{N}{2}-1}\left[x(n) + (-1)^s x\left(\frac{N}{2}+n\right)\right]W_N^{ns} W_{N/2}^{nr} \quad (5)$$

$$= DFT_{N/2}\left\{\left[x(n) + (-1)^s x\left(\frac{N}{2}+n\right)\right]W_N^{ns}\right\}$$

Equation (5) is the standard form for a decimation-in-frequency fast Fourier transform (FFT) in which Z=2. The even-numbered points X(0), X(2), X(4), . . . are determined from the N/2-pt DFT of the sequence x(n)+x(N/2+n), and the odd-numbered points X(1), X(3), X(5) . . . are determined from the N/2-pt DFT of the sequence [x(n)−x(N/2+n)]$W_N^n$. At this point, the decimation can be further continued by subdividing the input sequence by a factor a Z:

$$X(2r+s) = \quad (6)$$

$$\sum_{y=0}^{Z-1}\sum_{n=0}^{\frac{N}{2Z}-1}\left[x\left(\frac{yN}{2Z}+n\right)+(-1)^s x\left(\frac{N}{2}+\frac{yN}{2Z}+n\right)\right]W_N^{(\frac{yN}{2Z}+n)s} W_{N/2}^{(\frac{yN}{2Z}+n)r}$$

In a conventional decimation-in-frequency algorithm, the order of the two summations is interchanged, and the transform operation is reduced to a set of 2Z DFTs of length N/2Z. With respect to the volumetric PET data set, however, it is not possible to interchange the summations. Instead, the expression is reduced by substituting r=pZ+q(q∈[0,Z−1], p∈[0,N/(2Z)−1]):

$$X(2pZ+2q+s) = \quad (7)$$

$$\sum_{y=0}^{Z-1}\sum_{n=0}^{\frac{N}{2Z}-1}\left[x\left(\frac{yN}{2Z}+n\right)+(-1)^s x\left(\frac{N}{2}+\frac{yN}{2Z}+n\right)\right]W_N^{(\frac{yN}{2Z}+n)s} W_{N/2}^{(\frac{yN}{2Z}+n)(pZ+q)}$$

The second twiddle factor of equation (7) is then rearranged as:

$$W_{N/2}^{(\frac{yN}{2Z}+n)(pZ+q)} = W_{N/2}^{\frac{yNp}{2}} W_{N/2}^{npZ} W_{N/2}^{q(\frac{yN}{2Z}+n)} = 1 \cdot W_{N/2Z}^{np} W_N^{2q(\frac{yN}{2Z}+n)} \quad (8)$$

Substitution of this expression for the second twiddle factor from equation (7) into the transform equation yields equation (1):

$$X(2pZ+2q+s) = \sum_{y=0}^{Z-1}\sum_{n=0}^{\frac{N}{2Z}-1}\left[x\left(\frac{yN}{2Z}+n\right)+(-1)^s x\left(\frac{N}{2}+\frac{yN}{2Z}+n\right)\right] \quad (9)$$

$$W_N^{(\frac{yN}{2Z}+n)(2q+s)} W_{N/2Z}^{np}$$

$$= \sum_{y=0}^{Z-1} DFT_{N/2Z}\left\{\left[x\left(\frac{yN}{2Z}+n\right)+\right.\right.$$

$$\left.\left.(-1)^s x\left(\frac{N}{2}+\frac{yN}{2Z}+n\right)\right]W_N^{(\frac{yN}{2Z}+n)(2q+s)}\right\}$$

The values X(2q+s), X(2Z+2q+s), X(4Z+2q+s) . . . are the sum of the results of Z DFTs of N/2Z points. The entire X sequence is obtained with $2Z^2$ DFTs, where each DFT uses N/2Z consecutive points from the first half of the input sequence and N/2Z consecutive points from the second half of the input sequence. While this decimation procedure is less efficient than the standard DFT decimation algorithm, which would accomplish the same task with only 2Z DFTs, it permits the volumetric PET data to be used in the order in which it is stored, i.e., permits the use of data in the projection plane format. Consequently, there is no need to resort the volumetric PET data from the projection plane format produced by the sorter 34 into the cross-plane sinogram format, and so the time necessary for the resorting procedure is saved.

Figure 5:
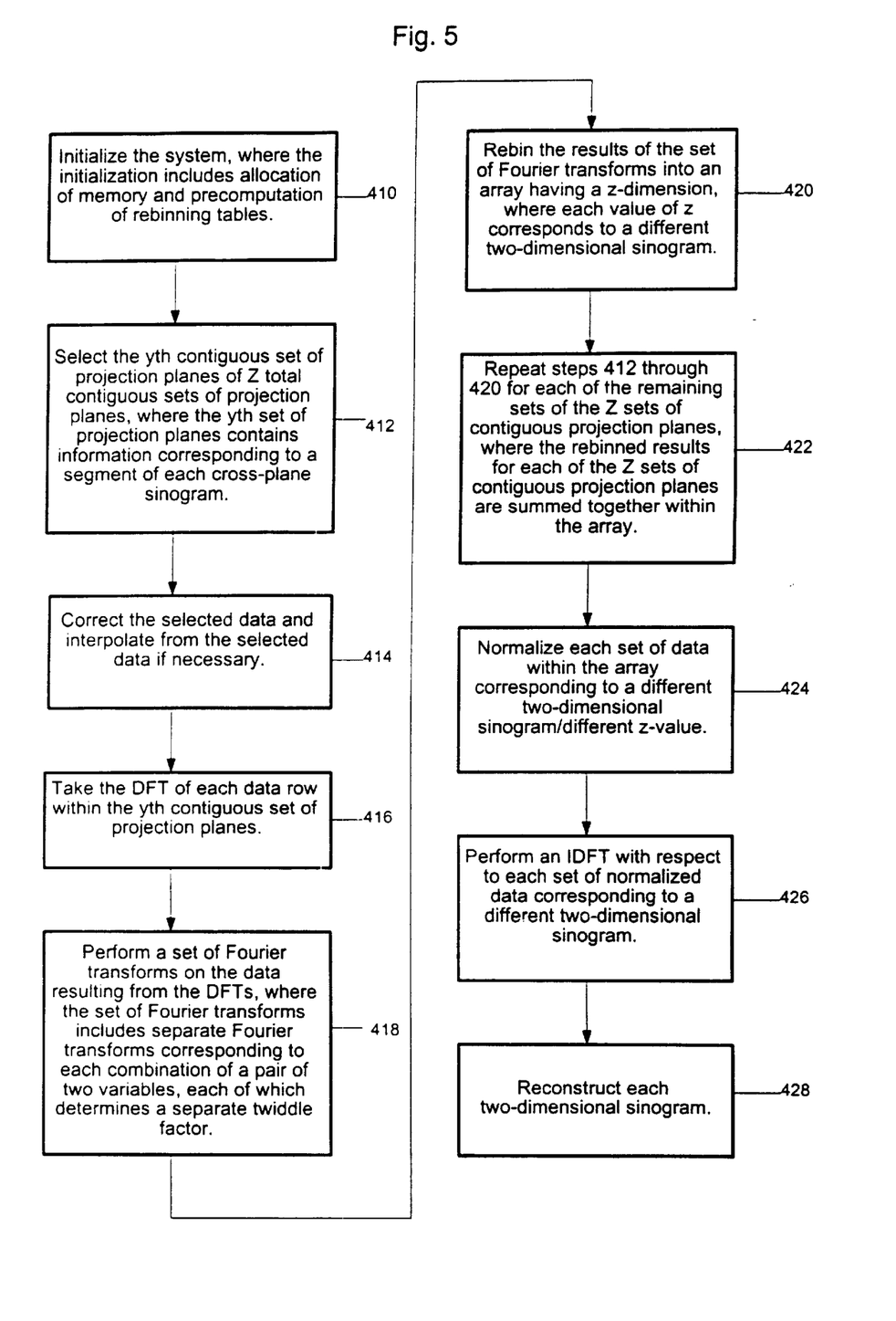
FIG. 5 is a flow chart showing exemplary method steps performed by one embodiment of the PET scanner system of FIG. 1.

Referring to FIG. 5, exemplary steps performed by the array processor 45 in converting the data from the projection plane format into the two-dimensional sinogram format without intermediate conversion to the cross-plane sinogram format, using the decimation technique of equation (1), are shown. Upon starting operation, an initialization procedure is performed by the array processor 45 at step 410. This initialization includes allocation of memory within the array processor 45, including memory for a normalized sinogram array P($\omega$, k, z), which is to hold information corresponding to a set of two-dimensional sinograms. The initialization further includes the precomputing of rebinning tables, which are used to perform the FORE algorithm.

Next, at step 412, the array processor 45 selects a contiguous set of projection planes from the overall projection plane data set provided by the sorter 34. The overall projection plane data set typically includes multiple sets of contiguous projection planes, e.g., Z total sets of contiguous projection planes. Contiguous sets of projection planes can be understood as sets of data that vary consecutively with respect to the variable $\phi$. Each contiguous set of projection planes further represents a segment of each cross-plane sinogram. The data from each of the sets of contiguous projection planes must be converted into the two-dimensional sinogram format in order to obtain the maximum amount of two-dimensional sinogram information. Consequently, as shown in step 422, steps 412–420 of FIG. 5 are repeated for each of the Z sets of contiguous projection planes, i.e., the steps are repeated for each y $\epsilon$0, Z–1.

After selecting a contiguous set of projection planes, the array processor 45 then reads and corrects the views required for that selected projection plane data, at step 414. Under certain circumstances, the array processor 45 also performs interpolation of the data if it is necessary. At step 416, the array processor 45 then takes the DFT of each data row within the selected projection plane data. By performing these DFTs, the variables r and $\phi$ of the original projection plane data are replaced by the variables $\omega$) and n in the transformed data set. The transformed data set is typically stored by the array processor 45 in an array and, in certain embodiments, the array processor 416 buffers the results corresponding to positive $\theta$ in one array $X_{+\theta}(\omega, n, v)$ and buffers the results from negative $\theta$ in a second array $X_{31\ \theta}(\omega, n, v)$.

At step 418, a set of Fourier transforms (typically, DFTs) are performed on the transformed data set. The set of Fourier transforms includes individual Fourier transforms corresponding to each combination of a pair of two indices, e.g., q and s. Each combination of the pair of two indices, determines a different twiddle factor employed in calculating the Fourier transforms. The Fourier transforms performed at step 418 employ equation (1) discussed above. Upon completion of the Fourier transforms of step 418, the results of the Fourier transforms are rebinned into the normalized sinogram array P($\omega$, k, z). The results obtained from the performing of successive Fourier transforms for the different values of y, $\theta$ ($\theta$ and v are discussed below with reference to FIG. 6), v, q and s are summed within the normalized sinogram array to produce overall totals within the normalized sinogram array once all of the Fourier transforms for all of the different combinations have been performed. The normalized sinogram array includes a dimension z, which corresponds to variation in the axial direction of the PET scanner. Thus, the data stored in the normalized sinogram array is indexed as pertaining to particular two-dimensional sinograms. Steps 418 and 420 are discussed in further detail with respect to FIG. 6.

Steps 412–420 are repeated for each of the contiguous sets of projection planes, at step 422. Once steps 412–420 have been performed with respect to all of the projection plane data, the array processor 45 proceeds to step 424, at which the array processor normalizes the data within the normalized sinogram array using a hits matrix. The hits matrix is calculated by the array processor 45 based upon the rebinning tables for each sinogram. In alternate embodiments, normalization can be obtained in other ways (e.g., by other calculations) besides the use of a hits matrix. Next, at step 426, the array processor 45 performs an inverse DFT with respect to each set of normalized data within the normalized sinogram array corresponding to a different two-dimensional sinogram, i.e., each set of data within the normalized sinogram array corresponding to a particular value of z. Once the inverse DFTs have been performed, the array processor 45 has access to data in the two-dimensional sinogram format and, at step 428, is able to reconstruct two-dimensional sinograms from which images can be generated.

Figure 6:
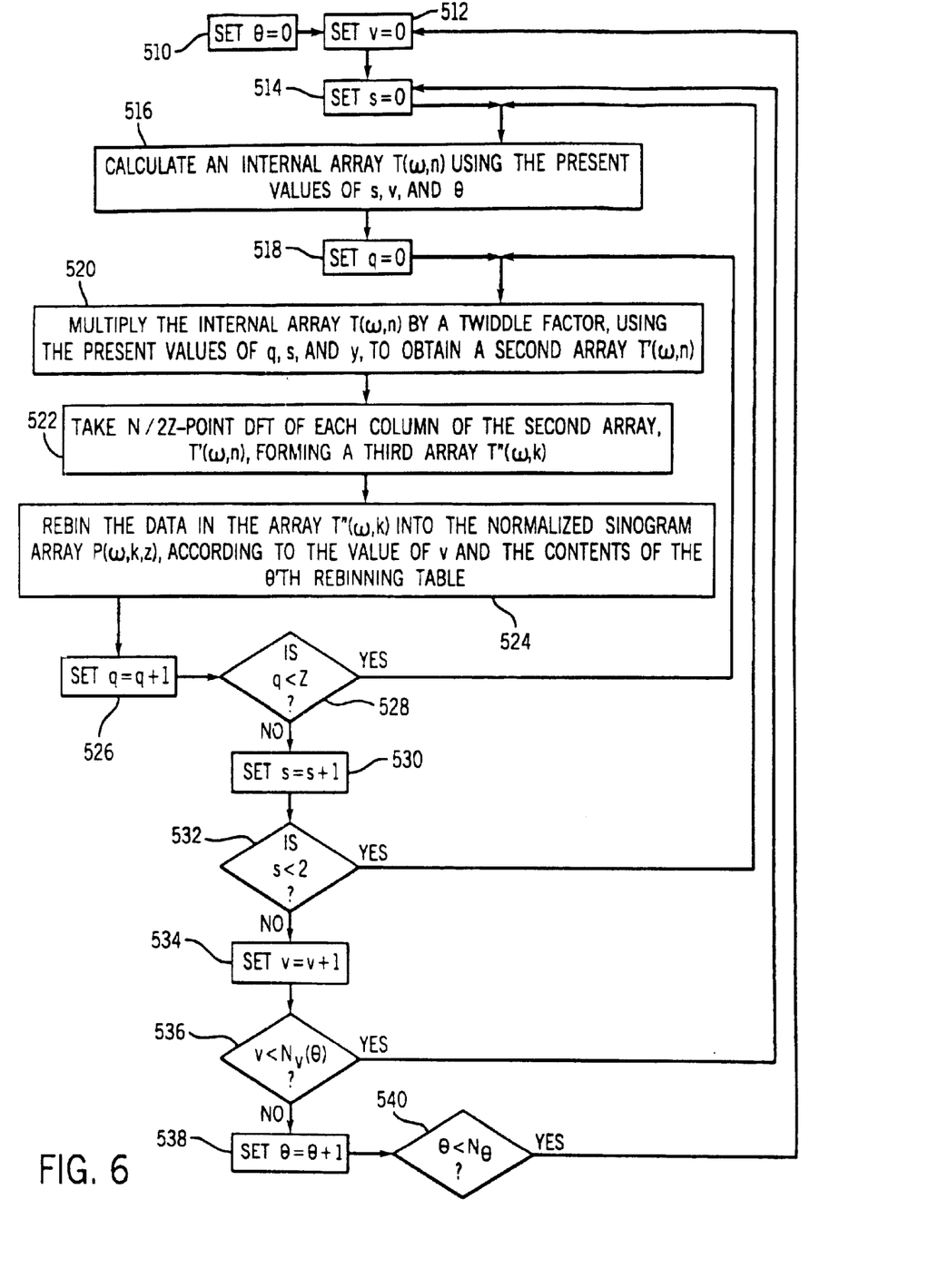
FIG. 6 is a flow chart showing in greater detail one embodiment of a portion of the flow chart of FIG. 5.

Turning to FIG. 6, in one embodiment of the invention, steps 418 and 420 of FIG. 5 include components or substeps 510–540. At steps 510, 512 and 514, respectively, the variables $\theta$, v and s are each set equal to zero. The variables $\theta$ and v identify information corresponding to particular cross-plane sinograms. At step 516, the array processor 45 then calculates a first internal array T($\omega$, n), using the present values of s, v and $\theta$, where the contents of the array are defined as T($\omega$, n)=$X_{+\theta}(\omega, n, v)+(-1)^s X_{31\ \theta}(\omega, n, v)$. The first internal array corresponds to the internal term of equation (1) that is shown in square brackets. Next, at step the array processor 45 sets the variable q equal to zero. The variables s and q are the same variables as shown in equation (1).

At step 520, the array processor 45 multiplies the first internal array T($\omega$, n) by the twiddle factor shown in equation (1), using the present values of q, s and y, to obtain a modified internal array T'($\omega$, n). As is evident from step 436, q takes on all values between 0 and Z–1. At step 522, the N/(2Z)-point DFT of each column of the modified internal array T'($\omega$, n) is calculated to generate an additional internal array T"($\omega$, k). Then, at step 524, the data in the additional internal array T"($\omega$, k) is rebinned into the normalized sinogram array P($\omega$, k, z) according to the present value of v and the contents of the $\theta$th rebinning table.

At step 526, the value of q is incremented, and then at step 528, array processor 45 determines whether the incremented value of q is still less than Z. If the value of q is still less than Z, the array processor 45 returns to step 520 to perform the same operations of steps 430 through 436 again. If q is no longer less than Z at step 528, the array processor 45 proceeds to step 530, at which the value of s is incremented. If at step 532 it is determined that s is equal to 1, the array processor 45 then returns to step 516 to reperform steps 516 through 530. If at step 532 it is determined that s is equal to 2, the array processor 45 then proceeds to step 534, at which the value of v is incremented.

If at step 536 it is determined that v is less than $N_v(\theta)$, then the array processor 45 returns to step 514 to reperform steps 514 through 534. If at step 536 it is determined that v is not less than $N_v(\theta)$, then the array processor 45 proceeds to step 538, at which the value of $\theta$ is incremented. The limit value for the variable v, $N_v$, depends upon $\theta$ because the area of an image plane becomes smaller as the axis of the plane (i.e., the axis perpendicular to the plane) becomes increasing parallel with respect to central axis 2 (i.e., as $\theta$ approaches 90°). If at step 540 it is determined that $\theta$ is less than $N_\theta$, the limit value for $\theta$, the array processor 45 returns to step 512 to reperform steps 512 through 538. If at step 540 it is determined that $\theta$ is not less than $N_\theta$, then the array processor 45 has completed the components of steps 418 and the array processor can return to step 422 of the flow chart of FIG. 5.

While the foregoing specification illustrates and describes the preferred embodiments of this invention, it is to be understood that the invention is not limited to the precise construction herein disclosed. The invention can be embodied in other specific forms without departing from the spirit or essential attributes. For example, the invention can be employed in hybrid PET scanners as well as strictly volumetric scanners. Accordingly, reference should be made to the following claims, rather than to the foregoing specification, as indicating the scope of the invention.

What is claimed is:

1. A method of processing data in a PET scanner wherein a projection plane data set is converted into a two-dimensional sinogram data set, the method comprising:

(1) selecting a subset of projection plane data from the projection plane data set;

(2) performing a set of Fourier transforms, respectively, on a plurality of data rows within the subset of projection plane data to obtain a transformed data set;

(3) performing an additional set of Fourier transforms on the transformed data set to obtain intermediate results, wherein the additional set of Fourier transforms includes a plurality of individual Fourier transforms respectively corresponding to a plurality of combinations of at least two indices;

(4) rebinning the intermediate results into a first array, the first array having at least a first dimension corresponding to a physical dimension of the PET scanner;

(5) repeating (1)–(4) for each of the remaining subsets of projection plane data, to provide a complete data set within the first array; and (6) performing a set of inverse Fourier transforms with respect to the complete data set to provide the two-dimensional sinogram data set.

2. The method of claim 1, further comprising:

(0) initializing a processing system within the PET scanner, wherein the initializing includes allocating memory and precomputing rebinning tables.

3. The method of claim 1, further comprising:

between (1) and (2), correcting the subset of projection plane data and, when necessary, interpolating from the subset of projection plane data.

4. The method of claim 1, wherein the first dimension corresponds to an axial dimension of the PET scanner.

5. The method of claim 1, wherein the intermediate results that are rebinned in each successive performance of (4) are summed within the first array with existing data within the first array.

6. The method of claim 1, further comprising:

prior to (6), normalizing the data within the first array.

7. The method of claim 1, further comprising:

(7) reconstructing a plurality of two-dimensional sinograms from the two-dimensional sinogram data set.

8. The method of claim 1, wherein (3) and (4) include:

(a) setting a first index, a second index and a third index equal to first, second and third initial values, respectively;

(b) calculating a second array, based upon current values of the first, second and third indices;

(c) setting a fourth index equal to a fourth initial value;

(d) performing a Fourier transform of each column of the second array to obtain a third array;

(e) rebinning the data of the third array into the first array;

(f) incrementing the value of the fourth index;

(g) repeating (d)–(f) until the value of the fourth index has reached a fourth limit;

(h) incrementing the values of the first, second and third indices; and (i) repeating (b)–(h) until the values of the first, second and third indices have reached first, second and third limits, respectively.

9. The method of claim 8, wherein (2) further comprises buffering a first subset of the transformed data set corresponding to a positive value of the first index in a fourth array, and buffering a second subset of the transformed data set corresponding to a negative value of the first index in a fifth array.

10. The method of claim 1, wherein the following equation is employed:

$$X(2pZ+2q+s) = \sum_{y=0}^{Z-1} DFT_{N/2Z}\left\{\left[x\left(\frac{yN}{2Z}+n\right) + (-1)^s x\left(\frac{N}{2}+\frac{yN}{2Z}+n\right)\right] W_N^{(\frac{yN}{2Z}+n)(2q+s)}\right\}.$$

11. The method of claim 1, wherein each Fourier transform that is performed is one of a discrete Fourier transform and a fast Fourier transform.

12. A method of processing data in a PET scanner wherein input data in a projection plane format is converted into output data in a two-dimensional sinogram format, the method comprising:

(1) performing a Fourier transform of a plurality of data rows within a projection plane data set to obtain a transformed data set;

(2) setting a first index, a second index and a third index equal to first, second and third initial values, respectively;

(3) calculating a first array, based upon the values of the first, second and third indices;

(4) setting a fourth index equal to a fourth initial value;

(5) performing a Fourier transform of each column of the first array to obtain a second array;

(6) rebinning the data of the second array into a third array;

(7) incrementing the value of the fourth index;

(8) repeating (5)–(7) until the value of the fourth index has reached a fourth limit;

(9) incrementing the values of the first, second and third indices; and (10) repeating (3)–(9) until the values of the first, second and third indices have reached first, second and third limits, respectively, wherein the data rebinned into the third array is converted into the output data in the two-dimensional sinogram format.

13. The method of claim 12, further comprising:

(0) selecting the projection plane data set from an overall projection plane data set;

(11) repeating steps (0)–(1 0) for each of a plurality of additional projection plane data sets selected from the overall projection plane data set, to provide a complete data set within the third array; and (12) performing an inverse Fourier transform with respect to the complete data set to provide a two-dimensional sinogram data set.

14. The method of claim 12, wherein (5) includes multiplying the internal array by a twiddle factor using the values of the second, third and fourth indices.

15. A PET scanner comprising:

a gantry;

a plurality of sets of detectors supported by the gantry, the detectors in each set being disposed in a plane and positioned around a central axis that intersects the plane, the plurality of sets of detectors being spaced along the central axis;

a coincidence detector that identifies coincidence events from events sensed by the detectors, and which is configured to provide coincidence event data in a projection plane format; and a processing means for converting the coincidence event data from the projection plane format into a two-dimensional sinogram format without conversion of the data from the projection plane format into a cross-plane sinogram format.

16. The PET scanner of claim 15, wherein the processing means converts the coincidence event data from the projection plane format into the two-dimensional sinogram format by:

performing a set of Fourier transforms on a transformed data set to obtain intermediate results, wherein the transformed data set is obtained by performing a Fourier transform of a subset of the data in the projection plane format, and wherein the set of Fourier transforms includes a plurality of individual Fourier transforms respectively corresponding to a plurality of combinations of at least two variables;

rebinning the intermediate results into a first array, the first array having at least a first dimension corresponding to a physical dimension of the PET scanner; and performing an inverse Fourier transform with respect to the intermediate results in the first array to provide data in the two-dimensional sinogram format.

17. The PET scanner of claim 15, wherein the processing means includes a sorter and an array processor.

18. An array processor comprising:

a first array, in which first and second subsets of transformed row data corresponding respectively to positive and negative values of a first index are stored, wherein the transformed row data is obtained by performing a first set of Fourier transforms with respect to a set of projection plane data;

a second array, in which the results of a second set of Fourier transforms performed upon the transformed row data are rebinned into a transformed sinogram format, wherein the second set of Fourier transforms includes individual Fourier transforms corresponding to each respective combination of a second index and a third index; and a memory in which the first and second arrays are stored.

* * * * *